United States Patent
Dahl et al.

(10) Patent No.: US 6,976,967 B2
(45) Date of Patent: Dec. 20, 2005

(54) APPARATUS AND METHOD FOR SENSING SPATIAL DISPLACEMENT IN A HEART

(75) Inventors: Roger Dahl, Andover, MN (US); Michael J. Kallok, New Brighton, MN (US); Steve Sundquist, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 480 days.

(21) Appl. No.: 10/079,172

(22) Filed: Feb. 19, 2002

(65) Prior Publication Data

US 2003/0158494 A1  Aug. 21, 2003

(51) Int. Cl.[7] .................. A61B 5/04; A61N 1/365
(52) U.S. Cl. ............................... 600/508; 607/17
(58) Field of Search .................. 607/6, 9, 17–20, 607/27–28; 600/508–509

(56) References Cited

U.S. PATENT DOCUMENTS

| | | | |
|---|---|---|---|
| 5,573,012 A | 11/1996 | McEwan | 128/782 |
| 6,272,371 B1 * | 8/2001 | Shlomo | 600/424 |
| 6,285,898 B1 | 9/2001 | Ben-Haim | 600/374 |
| 6,298,269 B1 * | 10/2001 | Sweeney | 607/28 |
| 6,299,583 B1 | 10/2001 | Eggers et al. | 600/526 |

FOREIGN PATENT DOCUMENTS

WO    WO 01/06920 A1   2/2001   ......... A61B 5/0275

* cited by examiner

*Primary Examiner*—Jeffrey R. Jastrzab
(74) *Attorney, Agent, or Firm*—Michael C. Soldner; Girma Wolde-Michael (57) ABSTRACT

An electrical lead includes an elongate body having a proximal end, and a sensing unit capable of resolving a change in a spatial configuration of the electrical lead. A medical device includes a control unit, an elongate body having a proximal end coupled with the control unit, and a sensing unit capable of resolving a change in a spatial configuration of the electrical lead and relating it to the amount of blood ejected from the heart. A method includes receiving a signal transmitted from a lead disposed within a heart and determining a change in a dimension of the heart, due to the heart beating, based upon the signal.

20 Claims, 7 Drawing Sheets

APPARATUS AND METHOD FOR SENSING SPATIAL DISPLACEMENT IN A HEART

FIELD OF THE INVENTION

This invention relates to a method and apparatus for sensing one or more spatial displacements in a heart.

DESCRIPTION OF THE RELATED ART

Methods have been developed over the years to monitor the heart's function and to deliver various stimuli thereto. For example, cardiac pacing systems may monitor the heart's rhythm by sensing electrical signals transmitted by cardiac nerves to the heart and propagates throughout the heart muscle. If, for example, the heart fails to beat for a predetermined period of time, a pacing signal may be transmitted to a portion of the heart. Further, if fibrillation is detected in a portion of the heart, a defibrillating shock may be transmitted to that part of the heart that is experiencing fibrillation.

Sensing the electrical signals transmitted by the cardiac nerves and which propagates through the heart muscle generally provides an indirect indication, rather than a direct indication, of the mechanical function of the heart. For example, by sensing electrical signals transmitted by cardiac nerves to the heart, an indication of the heart's mechanical function may be inferred; however, the heart's function is not directly measured.

For example, merely sensing that the heart is beating electrically may not provide sufficient information to determine whether the left ventricle is contracting, and thus outputting blood, a commensurate amount with that being outputted by the right ventricle. Further, it may be difficult to determine by using traditional methods whether each of the ventricles are in fact contracting in unison, thereby evenly distributing blood therefrom.

Qualitative and quantitative aspects of cardiac output relating to the pumping of the heart, capacity, heart rate and similar cardiac data need to be monitored to assess, diagnose and treat cardiac symptoms. A system that enables a reliable measurement of cardiac data is therefore critical in the provision of cardiac care.

Generally, cardiac data is measured with reference to electrical signals. A significant problem in sensing electrical signals is that they do not give any indication of the heart's pumping status. For example, electrical signals can be measured when the heart is in mechanical standstill.

The present invention is directed to overcoming, or at least reducing, the effects of one or more of the problems set forth above.

SUMMARY OF THE INVENTION

In one aspect of the present invention, an electrical lead is provided that includes an elongate body having a proximal end, and a sensing unit capable of resolving a change in a spatial configuration of the electrical lead.

In another aspect of the present invention, a medical device is provided that includes a control unit, an elongate body having a proximal end coupled with the control unit, and a sensing unit capable of resolving a change in a spatial configuration of the electrical lead.

In yet another aspect of the present invention, a method is provided that includes receiving a signal transmitted from a lead disposed within a heart and determining a change in a dimension of the heart, due to the heart beating, based upon the signal.

BRIEF DESCRIPTION OF THE DRAWINGS

The invention may be understood by reference to the following description taken in conjunction with the accompanying drawings, in which the leftmost significant digit(s) in the reference numerals denote(s) the first figure in which the respective reference numerals appear, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF SPECIFIC EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

Embodiments of the present invention provide for determining the function of a heart and, thus for determining problems associated with the function of the heart. A pacing and/or stimulation signal from an implantable medical device may be transmitted to a portion of the heart in response to a determination that one or more problems exist in the function of the heart.

Figure 1:
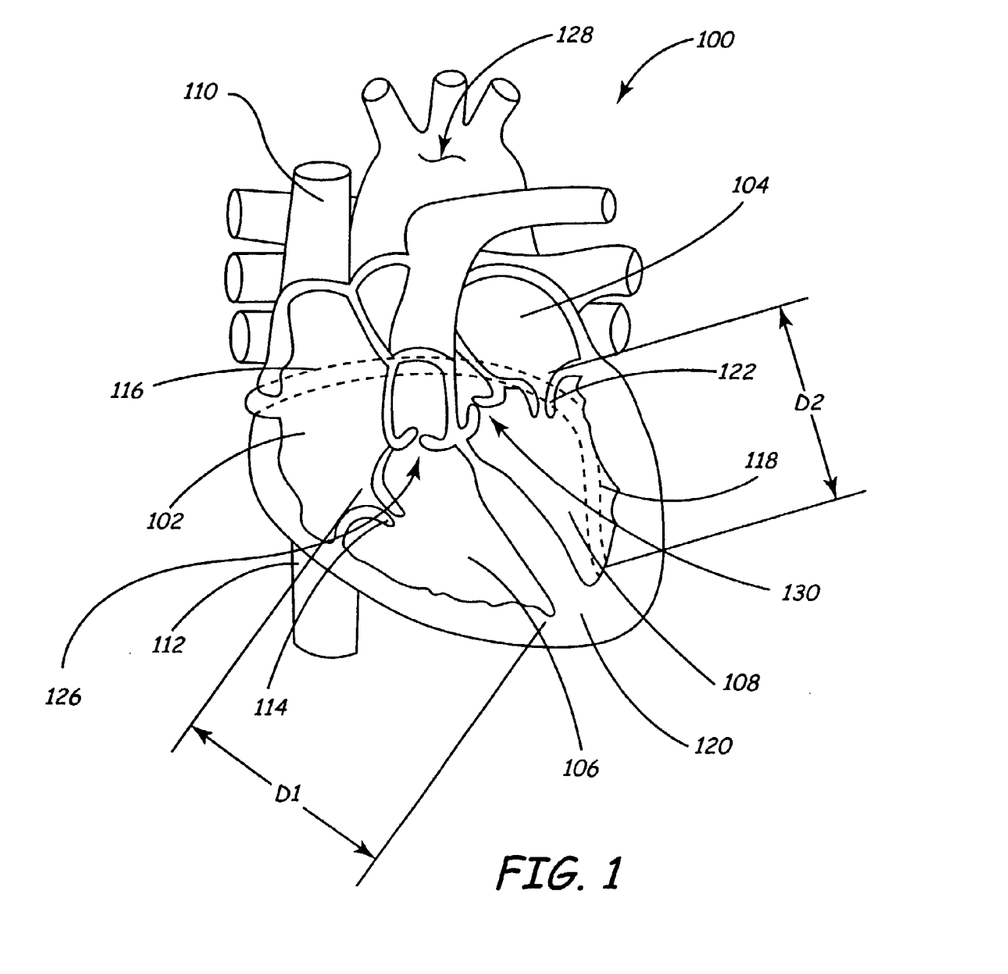
FIG. 1 is a stylized partial saggital cross sectional view of a human heart in diastole.

An anterior view of a human heart 100 is illustrated in FIG. 1. The heart 100 includes four chambers: a right atrium 102, a left atrium 104, a right ventricle 106, and a left ventricle 108. Extending into the right atrium 102 are a superior vena cava 110, which returns blood from the upper body, and an inferior vena cava 112, which returns blood from the lower body. Also extending into the right atrium, between an intersection between the inferior vena cava 112 and a tricuspid valve 114, is a coronary sinus 116. A middle cardiac vein 118 (shown in broken lines) leads from the apex 120 of the heart 100, around a posterior side of the heart 100, and ends in the coronary sinus 116. Blood from the heart 100 is returned via the middle cardiac vein 118 and other cardiac veins, through the coronary sinus 116, to the right atrium 102.

Still referring to FIG. 1, the tricuspid valve 114 separates the right atrium 102 and the right ventricle 106 and allows blood flow only from the right atrium 102 into the right ventricle 106. Similarly, the left atrium 104 is separated from the left ventricle 108 by a mitral valve 122, which allows blood flow only from the left atrium 104 into the left ventricle 108. Further, the right ventricle 106 is separated from a pulmonary artery 124 by a pulmonary valve 126, and the left ventricle is separated from an aorta 128 by an aortic valve 130. Each of the pulmonary valve 126 and the aortic valve 130 allow blood to pass from the right ventricle 106 and the left ventricle 108, respectively, and prevent blood from entering the right ventricle 106 and the left ventricle 108, respectively.

Figure 2:
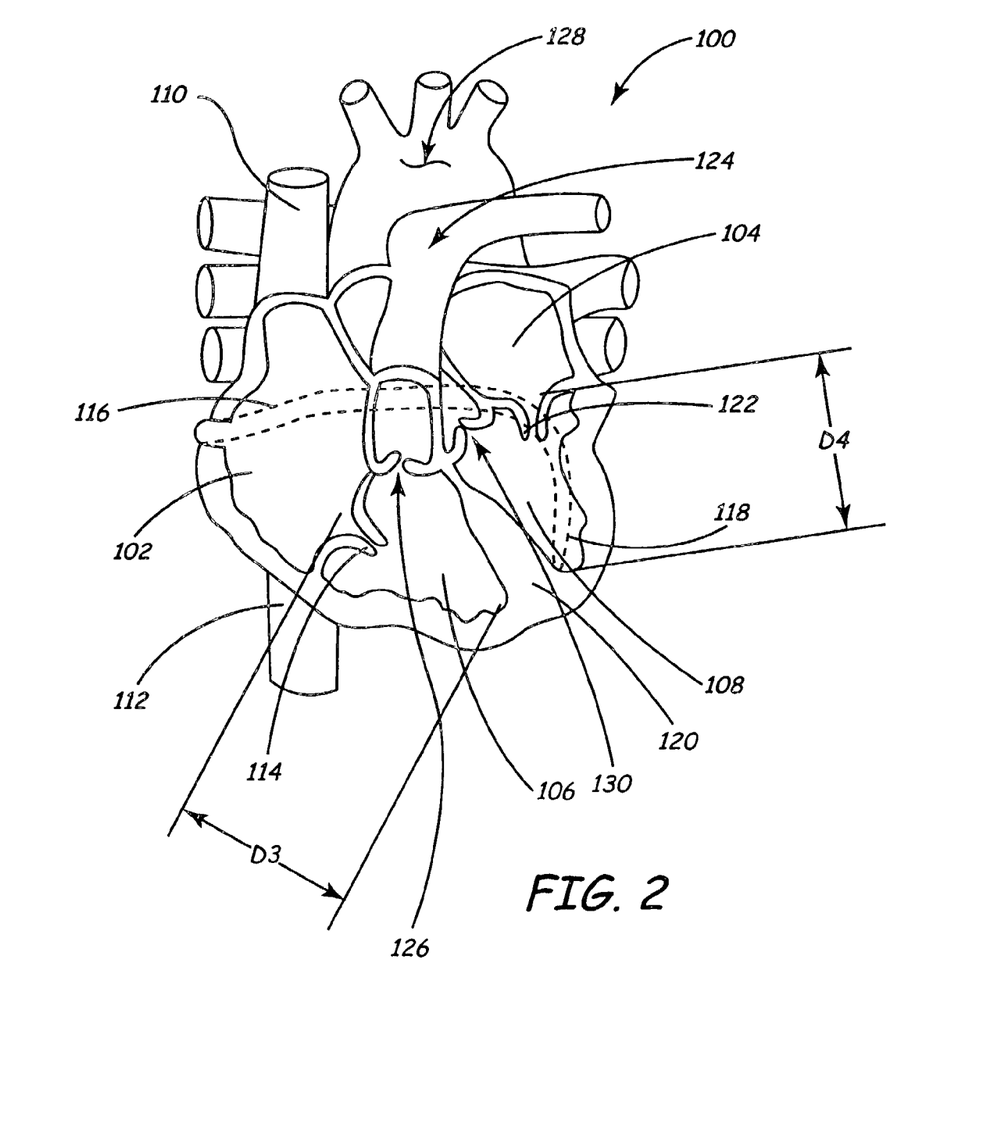
FIG. 2 is a stylized partial saggital cross sectional view of the human heart of FIG. 1 in systole.

During diastole, as illustrated in FIG. 1, the right atrium 102 and the left atrium 104 contract, forcing blood through the tricuspid valve 114 and the mitral valve 122, respectively, into the relaxed right ventricle 106 and the relaxed left ventricle 108, respectively. During systole, as illustrated in FIG. 2, the right ventricle 106 and the left ventricle 108 contract, forcing blood through the pulmonary valve 126 and the aortic valve 130, respectively, into the pulmonary artery 124 and the aorta 128, respectively. Also during systole, the right atrium 102 and the left atrium 104 relax, allowing blood to enter therein.

As the heart rhythm moves from diastole (shown in FIG. 1) to systole (shown in FIG. 2), a distance between the tricuspid valve 114 and the apex 120 of the heart 100 changes from a distance $D_1$ to a distance $D_3$, wherein the distance $D_3$ is smaller than the distance $D_1$. Similarly, a distance between the mitral valve 122 and the apex 120 of the heart 100 changes from a distance $D_2$ to a distance $D_4$ as the heart rhythm moves from diastole to systole. Again, the distance $D_4$ is smaller than the distance $D_2$. Therefore, the distance $D_1$ through $D_4$ may provide direct indications of the heart rhythm as it moves from diastole to systole. Thus, $\Delta D_{1,3}$ is the change in the distance $D_1$ to the distance $D_3$ through one heartbeat cycle and $\Delta D_{2,4}$ is the change in the distance $D_2$ to the distance $D_4$ through one heartbeat cycle.

By measuring the changes in these distances ($\Delta D_{1,3}$ and $\Delta D_{2,4}$) the function of the heart 100 may be directly monitored. For example, if $\Delta D_{1,3}$ and $\Delta D_{2,4}$ are both equal to or near zero, a conclusion may be made that both of the ventricles 106, 108 have stopped contracting and, in response, one or more pacing signals may be transmitted to the ventricles 106, 108 by the device. Further, if $\Delta D_{2,4}$ is equal to or near zero and $\Delta D_{1,3}$ is within an acceptable range, approximately 0.5 to 5 cm for the distances, it may be determined that the right ventricle 106 is contracting but the left ventricle 108 may not be adequately contracting. In such a situation, one or more pacing signals may be transmitted to the left ventricle 108. Conversely, if $\Delta D_{1,3}$ is equal to or near zero and $\Delta D_{2,4}$ is within the acceptable range (approximately 0.5 to 5 cm), it may be determined that the left ventricle 108 is contracting but the right ventricle 106 is not contracting. Thus, one or more pacing signals may be transmitted to the right ventricle 106.

If $\Delta D_{1,3}$ is small and changes rapidly over time, it may be determined that the heart 100 is fibrillating and, in response, a defibrillating shock may be applied by the device. Conversely, if $\Delta D_{2,4}$ is small and changes rapidly over time, it may be an indication of fibrillation and, in response, a defibrillating shock may be applied by the device. Should it be found that $\Delta D_{1,3}$ is smaller than a normal heart beat over several heartbeat cycles, it may be an indication that the heart 100 is experiencing tachycardia and, in response, a converting electrical shock and/or one or more pacing signals may be delivered by the device to the heart 100. Further, if $\Delta D_{2,4}$ is found to be smaller than a normal heart beat over several heartbeat cycles, the heart 100 may be experiencing tachycardia and, in response, a converting electrical shock and/or one or more pacing signals may be delivered to the left ventricle 108. The present invention also encompasses the determination of other cardiac conditions based upon one or more values of $\Delta D_{1,3}$ and $\Delta D_{2,4}$ over time. It should be noted that generally ventricular tends to fibrillate in unison and not independent of each other. Accordingly, although both left and right side leads 302, 304 are implemented in the context of the present invention, only one lead and associated flexural changes is sufficient to predict fibrillation or tachyarrythmias.

Figure 3:
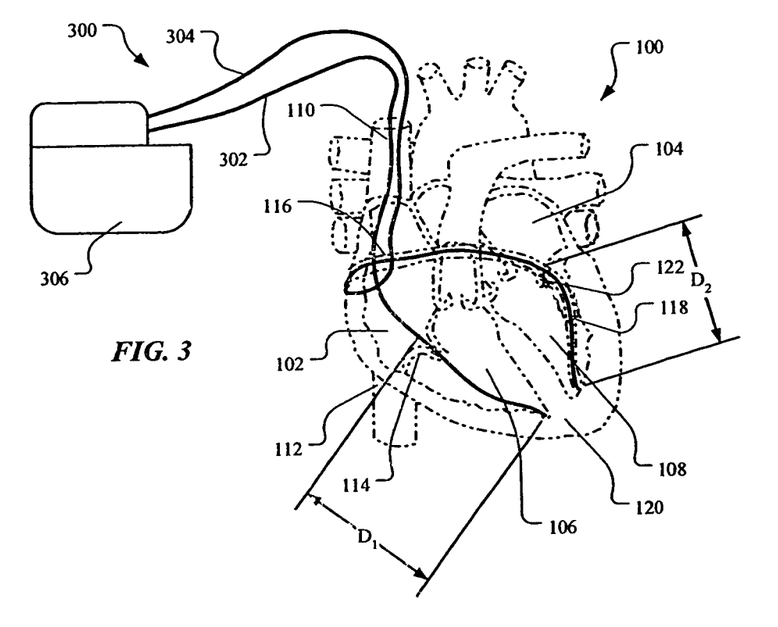
FIG. 3 is a stylized view of a medical device according to the present invention with electrical leads implanted in the human heart of FIG. 1.

FIG. 3 illustrates one embodiment of a medical device 300 according to the present invention. The medical device 300 includes a first lead 302 and a second lead 304 extending from a control unit 306. The control unit 306 may be capable of a variety of functions, e.g., transmitting pacing signals to one or more of the leads 302, 304, transmitting defibrillation pulses to one or more of the leads 302, 304, and/or receiving sensed signals from one or more of the leads 302, 304. In the illustrated embodiment, the first lead 302 may be routed into the heart 100 (shown in phantom) via the body's venous system (e.g., a subclavian vein or the like), through the superior vena cava 110, the right atrium 102, the tricuspid valve 114, and into the right ventricle 106. The second lead 304 may be routed into the heart 100 via the body's venous system (as with the first lead 302) through the superior vena cava 110, the right atrium 102, the coronary sinus 116, and into the middle cardiac vein 118. In one embodiment, the first lead 302 may be anchored to the superior vena cava 110, and/or right apex 120, and the second lead 304 may be anchored to either the coronary sinus 116 and/or the middle cardiac vein 118 to retain the leads 302, 304 in position.

As the heart rhythm moves from diastole (shown in FIG. 3) to systole (shown in FIG. 4), the shapes of the leads 302, 304 are changed corresponding to the distance changes $\Delta D_{1,3}$ and $\Delta D_{1,4}$, respectively. Each of the leads 302, 304 are capable of sensing the distance changes $\Delta D_{1,3}$ and $\Delta D_{2,4}$, respectively, and transmitting signals representative of these changes to the control unit 306. Thus, the function of the heart 100 may be directly monitored by sensing the distance changes $\Delta D_{1,3}$ and $\Delta D_{2,4}$.

Figure 4:
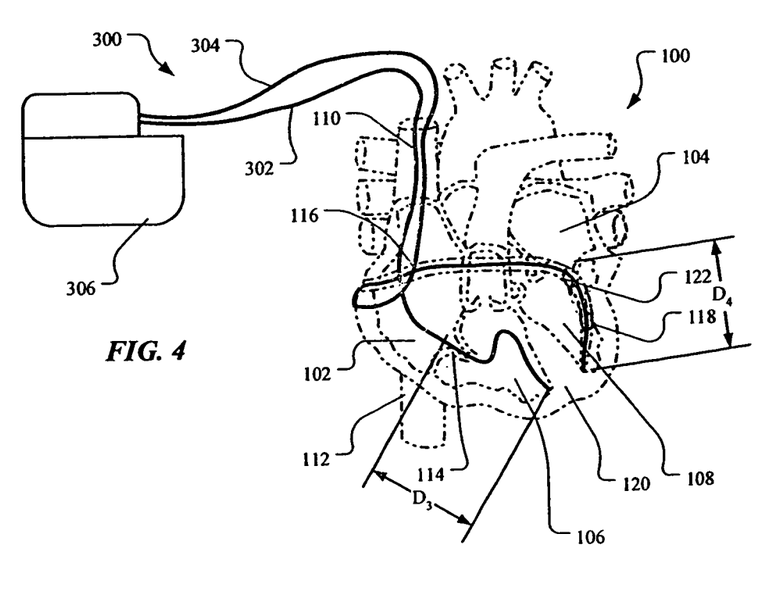
FIG. 4 is a stylized view of a medical device according to the present invention with electrical leads implanted in the human heart of FIG. 2.
Figure 5:
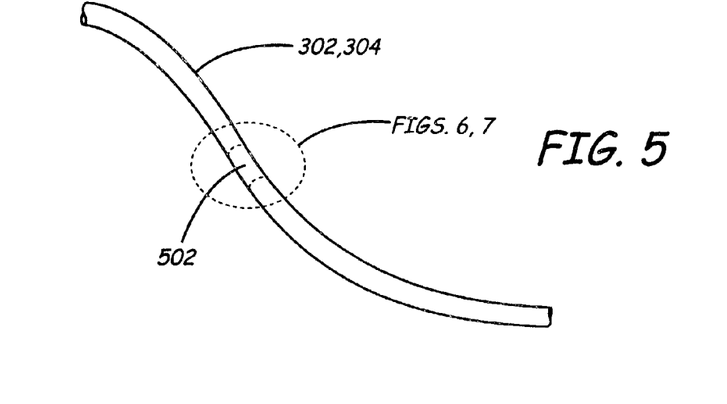
FIG. 5 is a stylized perspective view of a first embodiment of a lead according to the present invention.
Figures 6, 7:
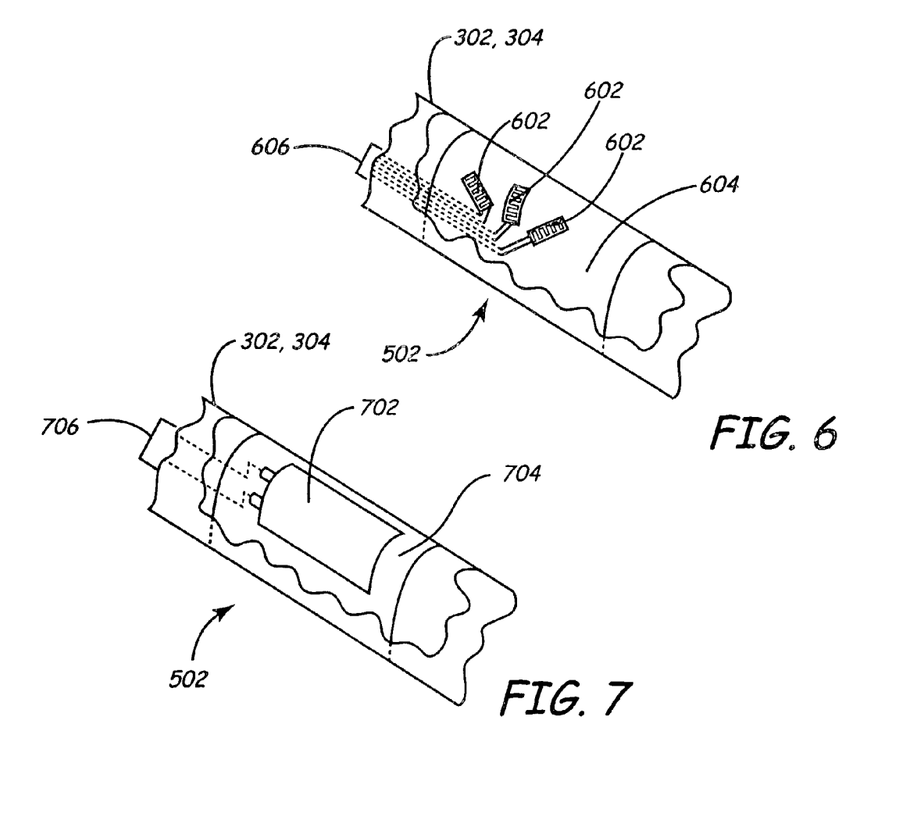
FIG. 6 is a stylized partial cross sectional perspective view of a first embodiment of the sensing element of FIG. 5.
FIG. 7 is a stylized partial cross sectional perspective view of a second embodiment of the sensing element of FIG. 5.

FIGS. 5 and 6 illustrate a first embodiment of the leads 302, 304 according to the present invention in which each of the leads 302, 304 includes one or more sensing elements 502 capable of sensing bending stress induced in the leads 302, 304. In one embodiment, the bending stress induced in the leads 302, 304 may be caused by changes in dimensions (e.g., $D_1$, $D_2$, $D_3$, $D_4$, or the like) as the heart 100 beats. In the embodiment illustrated in FIG. 6, the sensing element 502 includes a plurality of strain gauges 602 mounted to a substrate 604. While three strain gauges 602 are illustrated in FIG. 6, the use of any desired number or configuration of strain gauges 602 is encompassed by the present invention. Conductors 606 may originate from the strain gauges 602 to electrically couple the strain gauges 602 and the control unit 306 (shown in FIGS. 3 and 4) and, further, to provide electrical power to the strain gauges 602. The leads 302, 304 flex as the heart 100 beats, causing changes in resistivity in one or more of the strain gauges 602 corresponding to the direction and amount of flexing in the leads 302, 304. These changes in resistivity produce a corresponding change in voltage that can be processed by the control unit 306 to determine the distance changes $\Delta D_{1,3}$ and $\Delta D_{2,4}$ resulting from the beating of the heart 100.

FIGS. 5 and 7 illustrate a second embodiment of the leads 302, 304 according to the present invention, in which each of the leads 302, 304 includes one or more sensing elements 502 capable of sensing bending stress induced in the leads 302, 304. In one embodiment, the bending stress induced in the leads 302, 304 may be caused by changes in dimensions (e.g., $D_1$, $D_2$, $D_3$, $D_4$, or the like) as the heart 100 beats. In the embodiment illustrated in FIG. 7, the sensing element 502 includes one or more piezoresistive elements 702 mounted to a substrate 704. While one piezoresistive element 702 is illustrated in FIG. 7, the use of any desired number or configuration of piezoresistive elements 702 is encompassed by the present invention. Conductors 706 may originate from the piezoresistive element 702 to electrically couple the piezoresistive element 702 and the control unit 306 (shown in FIGS. 3 and 4) and, further, to provide electrical power to the piezoresistive element 702. The leads 302, 304 flex as the heart 100 beats, causing changes in resistivity in the piezoresistive element 702 corresponding to the direction and amount of flexing in the leads 302, 304. These changes in resistivity produce a corresponding change in voltage that can be processed by the control unit 306 to determine the distance changes $\Delta D_{1,3}$ and $\Delta D_{2,4}$ resulting from the heart 100 beating.

Figure 8:
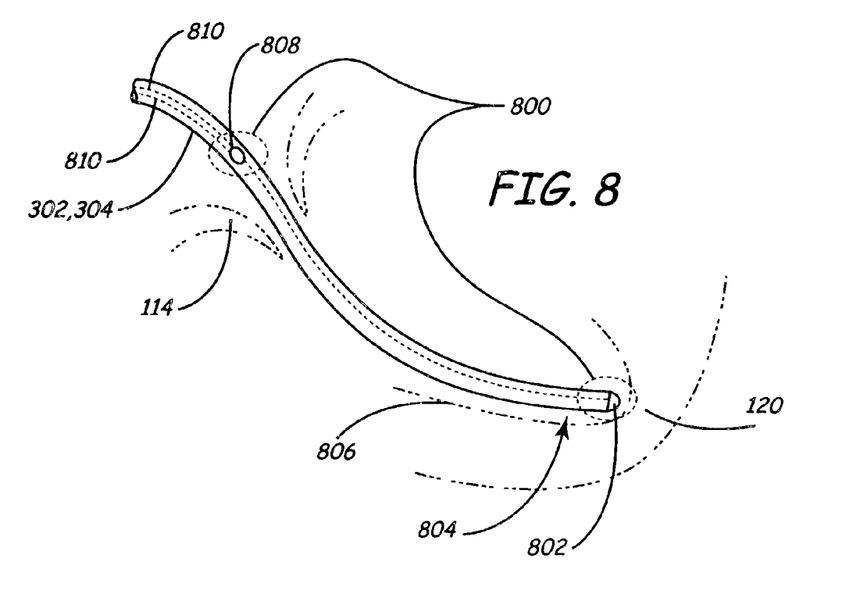
FIG. 8 is a stylized perspective view of a second embodiment of a lead according to the present invention.

A third embodiment of the leads 302, 304 according to the present invention is illustrated in FIG. 8. The leads 302, 304 include a sensing unit 800 having a first ultrasonic element 802 that is disposed proximate an end portion 804 of the lead. The sensing unit 800 further includes a second ultrasonic element 808 that is disposed intermediate the first ultrasonic element 802 and the control unit 306 (shown in FIGS. 3 and 4). In one embodiment, the first ultrasonic element 802 emits ultrasonic energy, which may be transmitted through the heart 100 towards, and received by, the second ultrasonic element 808. Alternatively, the second ultrasonic element 808 emits ultrasonic energy, which may be transmitted through the heart 100 towards, and received by, the first ultrasonic element 802. One or more conductors 810 extend from each of the first ultrasonic element 802 and the second ultrasonic element 808 to electrically couple the ultrasonic elements 802, 808 with the control unit 306 to provide power to the ultrasonic elements 802, 808 and, further, to transmit signals sent between the ultrasonic elements 802, 808 and the control unit 306.

In one embodiment, the leads 302 may be placed within the heart 100 such that the first ultrasonic element 802 is disposed 304 proximate an interior wall portion 806 of the apex 120 of the heart 100 (shown in FIGS. 3 and 4) and such that the second ultrasonic element 808 is disposed proximate the tricuspid valve 114. As the heart 100 beats, the distance between the first ultrasonic element 802 and the second ultrasonic element 808 changes, which is reflected by the signal transmitted from the receiving one of the ultrasonic elements 802, 808. The signal from the receiving one of the ultrasonic elements 802, 808 can be processed by the control unit 306 to determine the distance change $\Delta D_{1,3}$ resulting from the heart 100 beating.

Referring to FIGS. 3, 4, and 8, the second lead 304 may be routed into the coronary sinus 116 and into the middle cardiac vein 118 such that the first ultrasonic element 802 is disposed proximate the apex 120 of the heart 100 and such that the second ultrasonic element 808 is disposed proximate the mitral valve 122. As the heart 100 beats, the distance between the first ultrasonic element 802 and the second ultrasonic element 808 changes, which is reflected by the signal transmitted from the receiving one of the ultrasonic elements 802, 808. The signal from the receiving one of the ultrasonic elements 802, 808 can be processed by the control unit 306 to determine the distance change $\Delta D_{2,4}$ resulting from the heart 100 beating. The leads 302, 304, however, may be used in conjunction with any valve or other structure in the heart 100.

Figure 9:
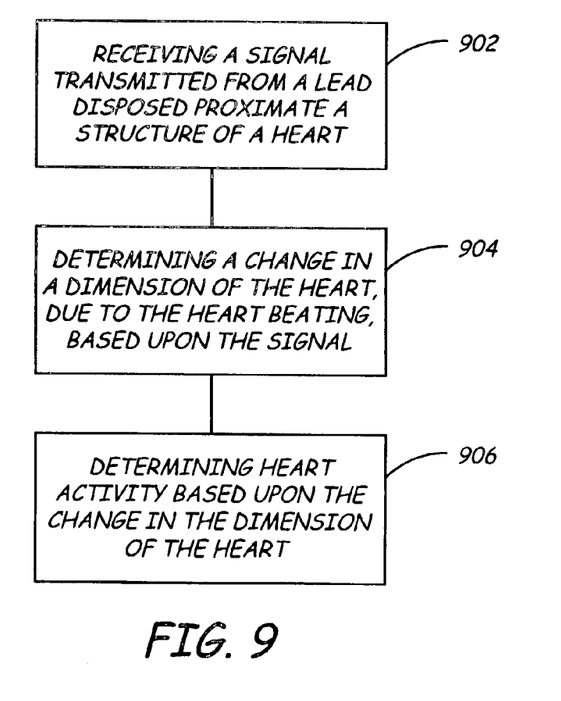
FIG. 9 is a flow chart of a first embodiment of a method according to the present invention.
Figure 10:
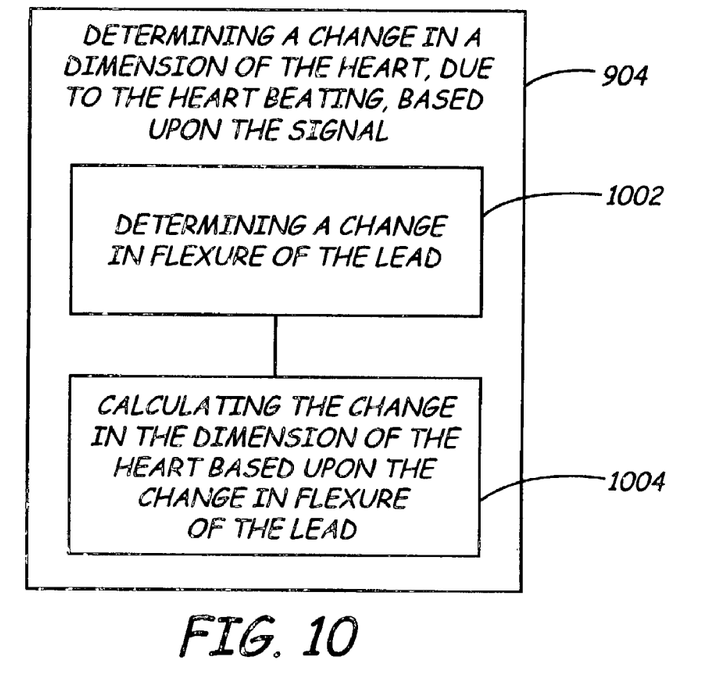
FIG. 10 is a flow chart of a second embodiment of a method according to the present invention.

FIG. 9 illustrates an embodiment of a method according to the present invention, which includes receiving a signal transmitted from a lead disposed proximate a structure of a heart (block 902) and determining a change in a dimension of the heart, due to the heart beating, based upon the signal (block 904). Further, the method may include determining heart activity based upon the change in the dimension of the heart (block 906). In one embodiment, illustrated in FIG. 10, determining the change in the dimension of the heart (block 904) further comprises determining a change in flexure in the lead (block 1002) and calculating the change in the dimension of the heart based upon the change in flexure in the lead (block 1004).

Figure 11:
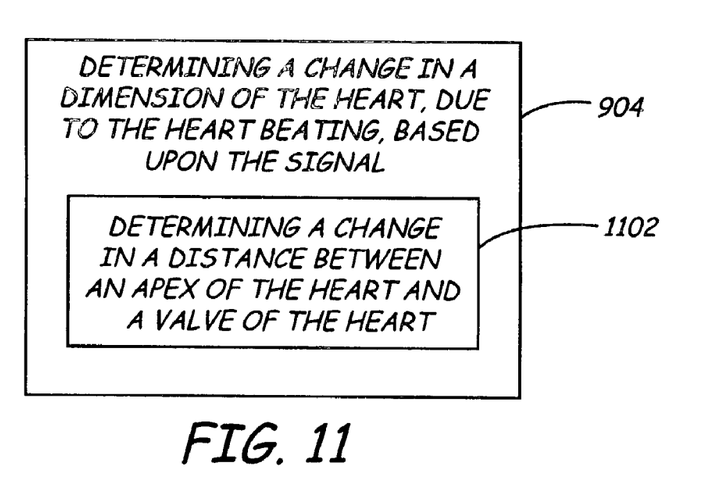
FIG. 11 is a flow chart of a third embodiment of a method according to the present invention.

FIG. 11 illustrates another embodiment of a method according to the present invention, in which determining the change in the dimension of the heart (block 904) further comprises determining a change in a distance between an apex of the heart and a valve of the heart (block 1102). Determining the change in the distance between the apex of the heart and the valve of the heart (block 1102) may include determining a change in a distance between the apex of the heart and one or more of a tricuspid valve and a mitral valve of the heart.

Figure 12:
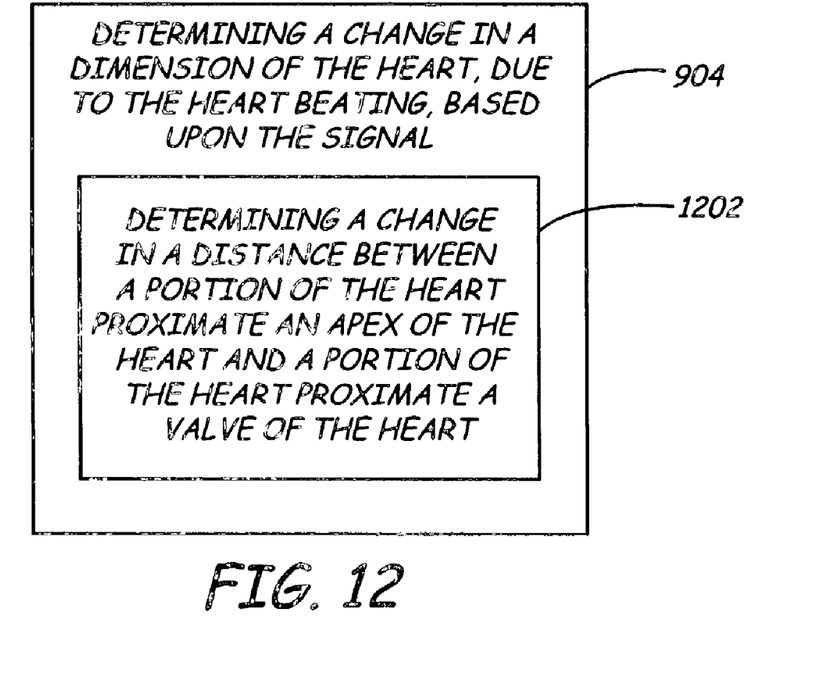
FIG. 12 is a flow chart of a fourth embodiment of a method according to the present invention.

In another embodiment, as illustrated in FIG. 12, determining the change in the dimension of the heart (block 904) may include determining a change in a distance between a portion of the heart proximate an apex of the heart and a portion of the heart proximate a valve of the heart (block 1202). Determining a change in a distance between a portion of the heart proximate an apex of the heart and a portion of the heart proximate a valve of the heart (block 1202) may include determining a change in a distance between the portion of the heart proximate an apex of the heart and a portion of the heart proximate a tricuspid valve of the heart. Further, determining a change in a distance between a portion of the heart proximate an apex of the heart and a portion of the heart proximate a valve of the heart (block 1202) may include determining a change in a distance between the portion of the heart proximate the apex of the heart and a portion of the heart proximate a mitral valve of the heart.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. An electrical lead adapted to be routed into a heart through a venous system of a body, comprising:
    an elongate body adapted to be anchored to a portion of the heart to retain the lead in position; and
    a sensing unit capable of resolving a change in a spatial configuration of the electrical lead, wherein the sensing unit of the electrical lead is capable of resolving a change in a spatial configuration of the electrical lead that is functionally related to a change in one of the following: (1) the distance between a tricuspid valve in the heart and an apex of the heart and (2) the distance between a mitral valve of the heart and the apex of the heart.

2. An electrical lead, according to claim 1, wherein the sensing unit further comprises:
    a substrate;
    a strain gauge mounted to the substrate and being capable of sensing a flexural stress induced in the electrical lead; and
    a plurality of conductors extending from the strain gauge toward the proximal end of the electrical lead.

3. An electrical lead, according to claim 1, wherein the sensing unit further comprises:
    a substrate;
    a plurality of strain gauges mounted to the substrate in a pattern and being capable of sensing a flexural stress induced in the electrical lead; and
    a plurality of conductors extending from the plurality of strain gauges toward the proximal end of the electrical lead.

4. An electrical lead, according to claim 1, wherein the sensing unit further comprises:
    a substrate;
    a piezoresistive element mounted to the substrate and being capable of sensing a bending stress induced in the electrical lead; and
    a plurality of conductors extending from the piezoresistive element toward the proximal end of the electrical lead.

5. An electrical lead, according to claim 1, wherein the electrical lead is adapted to be anchored in a portion of the heart selected from a group consisting of the superior vena cava, the right apex, the coronary sinus, and the middle cardiac vein.

6. An electrical lead, according to claim 1 wherein the sensing unit further comprises:
    a first ultrasonic element disposed proximate and adjoined to a distal end portion of the elongate body;
    a second ultrasonic element adjoined to the elongate body and disposed intermediate the first ultrasonic element and the proximal end portion of the elongate body; and
    a plurality of conductors extending from each of the first ultrasonic element and the second ultrasonic element toward the proximal end of the electrical lead.

7. An electrical lead, according to claim 1, wherein the sensing unit further comprises:
    a first ultrasonic element disposed proximate and adjoined to a distal end portion of the elongate body and being capable of emitting ultrasonic energy;
    a second ultrasonic element adjoined to the elongate body and disposed intermediate the first ultrasonic element and the proximal end portion of the elongate body, wherein the second ultrasonic element is capable of receiving at least a portion of the ultrasonic energy emitted by the first ultrasonic element; and
    a plurality of conductors extending from each of the first ultrasonic element and the second ultrasonic element toward the proximal end of the electrical lead.

8. An electrical lead, according to claim 1, wherein the sensing unit further comprises:
    a first ultrasonic element disposed proximate and adjoined to a distal end portion of the elongate body;
    a second ultrasonic element adjoined to the elongate body and disposed intermediate the first ultrasonic element and the proximal end portion of the elongate body, wherein the second ultrasonic element is capable of emitting ultrasonic energy; and
    a plurality of conductors extending from each of the first ultrasonic element and the second ultrasonic element toward the proximal end of the electrical lead,
    wherein the first ultrasonic element is capable of receiving at least a portion of the ultrasonic energy emitted by the second ultrasonic element.

9. An electrical lead, according to claim 1, wherein the sensing unit further comprises:
    a first ultrasonic element disposed proximate and adjoined to a distal end portion of the elongate body such that the first ultrasonic element may be placed within a heart proximate an apex of the heart;
    a second ultrasonic element adjoined to the elongate body and disposed intermediate the first ultrasonic element and the proximal end portion of the elongate body such that the second ultrasonic element may be placed within the heart proximate a tricuspid valve of the heart; and
    a plurality of conductors extending from each of the first ultrasonic element and the second ultrasonic element toward the proximal end of the electrical lead.

10. An electrical lead, according to claim 1, wherein the sensing unit further comprises:
    a first ultrasonic element disposed proximate and adjoined to a distal end portion of the elongate body such that the first ultrasonic element may be placed within a coronary vein proximate an apex of the heart;
    a second ultrasonic element adjoined to the elongate body and disposed intermediate the first ultrasonic element and the proximal end portion of the elongate body such that the second ultrasonic element may be placed within the coronary vein proximate a mitral valve of the heart; and
    a plurality of conductors extending from each of the first ultrasonic element and the second ultrasonic element toward the proximal end of the electrical lead.

11. A medical device, comprising:
    a control unit;
    an electrical lead having an elongate body with a proximal end coupled with the control unit, said lead being adapted to be routed into a heart through a venous system of a body and adapted to be anchored to a portion of the heart to retain the lead in position; and a sensing unit capable of resolving a change in a spatial configuration of the electrical lead, wherein the sensing unit of the electrical lead is capable of resolving a change in a spatial configuration of the electrical lead that is functionally related to a chance in one of the following: (1) the distance between a tricuspid valve in the heart and an apex of the heart and (2) the distance between a mitral valve of the heart and the apex of the heart.

12. A medical device, according to claim 11, wherein the sensing unit further comprises:
a substrate;
a strain gauge mounted to the substrate and being capable of sensing a bending stress induced in the electrical lead; and
a plurality of conductors extending from the strain gauge and electrically coupled with the control unit.

13. A medical device, according to claim 11, wherein the sensing unit further comprises:
a substrate;
a plurality of strain gauges mounted to the substrate in a rosette pattern and being capable of sensing a bending stress induced in the electrical lead; and
a plurality of conductors extending from the plurality of strain gauges and electrically coupled with the control unit.

14. A medical device, according to claim 11, wherein the sensing unit further comprises:
a substrate;
a piezoresistive element mounted to the substrate and being capable of sensing a bending stress induced in the electrical lead; and
a plurality of conductors extending from the piezoresistive element and electrically coupled with the control unit.

15. A medical device, according to claim 11, wherein the electrical lead is adapted to be anchored in a portion of the heart selected from a group consisting of the superior vena cava, the right apex, the coronary sinus, and the middle cardiac vein.

16. A medical device, according to claim 11, wherein the sensing unit further comprises:
a first ultrasonic element disposed proximate and adjoined to a distal end portion of the elongate body;
a second ultrasonic element adjoined to the elongate body and disposed intermediate the first ultrasonic element and the proximal end portion of the elongate body; and
a plurality of conductors extending from each of the first ultrasonic element and the second ultrasonic element and electrically coupled with the control unit.

17. A medical device, according to claim 11, wherein the sensing unit further comprises:
a first ultrasonic element disposed proximate and adjoined to a distal end portion of the elongate body and being capable of emitting ultrasonic energy;
a second ultrasonic element adjoined to the elongate body and disposed intermediate the first ultrasonic element and the proximal end portion of the elongate body, wherein the second ultrasonic element is capable of receiving at least a portion of the ultrasonic energy emitted by the first ultrasonic element; and
a plurality of conductors extending from each of the first ultrasonic element and the second ultrasonic element and electrically coupled with the control unit.

18. A medical device, according to claim 11, wherein the sensing unit further comprises:
a first ultrasonic element disposed proximate and adjoined to a distal end portion of the elongate body;
a second ultrasonic element adjoined to the elongate body and disposed intermediate the first ultrasonic element and the proximal end portion of the elongate body, wherein the second ultrasonic element is capable of emitting ultrasonic energy; and
a plurality of conductors extending from each of the first ultrasonic element and the second ultrasonic element and electrically coupled with the control unit,
wherein the first ultrasonic element is capable of receiving at least a portion of the ultrasonic energy emitted by the second ultrasonic element.

19. A medical device, according to claim 11, wherein the sensing unit further comprises:
a first ultrasonic element disposed proximate and adjoined to a distal end portion of the elongate body such that the first ultrasonic element may be placed within a heart proximate an apex of the heart;
a second ultrasonic element adjoined to the elongate body and disposed intermediate the first ultrasonic element and the proximal end portion of the elongate body such that the second ultrasonic element may be placed within the heart proximate a tricuspid valve of the heart; and
a plurality of conductors extending from each of the first ultrasonic element and the second ultrasonic element and electrically coupled with the control unit.

20. A medical device, according to claim 11, wherein the sensing unit further comprises:
a first ultrasonic element disposed proximate and adjoined to a distal end portion of the elongate body such that the first ultrasonic element may be placed within a coronary vein proximate an apex of the heart;
a second ultrasonic element adjoined to the elongate body and disposed intermediate the first ultrasonic element and the proximal end portion of the elongate body such that the second ultrasonic element may be placed within the coronary vein proximate a mitral valve of the heart; and
a plurality of conductors extending from each of the first ultrasonic element and the second ultrasonic element and electrically coupled with the control unit.

* * * * *